United States Patent
Steffan et al.

(10) Patent No.: US 6,344,451 B1
(45) Date of Patent: Feb. 5, 2002

(54) PYRROLOBENZODIAZEPINE CARBOXAMIDE VASOPRESSIN AGONISTS

(75) Inventors: Robert J. Steffan, Langhorne, PA (US); Amedeo A. Failli, Princeton Junction, NJ (US)

(73) Assignee: American Home Products, Madison, NJ (US)

( * ) Notice: Subject to any disclaimer, the term of this patent is extended or adjusted under 35 U.S.C. 154(b) by 0 days.

(21) Appl. No.: 09/495,506

(22) Filed: Feb. 1, 2000

Related U.S. Application Data

(60) Provisional application No. 60/155,189, filed on Feb. 4, 1999, now abandoned.

(51) Int. Cl.⁷ ............... A61K 31/55; C07D 487/12; A61P 7/12
(52) U.S. Cl. ................... 514/220; 540/561
(58) Field of Search ............. 540/561; 514/220

(56) References Cited

U.S. PATENT DOCUMENTS

| | | | |
|---|---|---|---|
| 4,766,108 A | 8/1988 | Ali ............... | 514/16 |
| 5,055,448 A | 10/1991 | Manning et al. ...... | 514/16 |
| 5,070,187 A | 12/1991 | Gavras et al. ...... | 530/315 |
| 5,512,563 A | 4/1996 | Albright et al. ...... | 514/217 |
| 5,516,774 A | 5/1996 | Albright et al. ...... | 514/220 |
| 5,521,173 A | 5/1996 | Venkatesan et al. .... | 514/220 |
| 5,624,923 A | 4/1997 | Albright et al. ...... | 514/220 |
| 5,733,905 A | 3/1998 | Albright et al. ...... | 514/220 |
| 5,736,540 A | 4/1998 | Albright et al. ...... | 514/220 |

FOREIGN PATENT DOCUMENTS

| | | |
|---|---|---|
| EP | 0636625 | 2/1995 |
| EP | 0640592 | 3/1995 |
| JP | 08081460 | 3/1996 |
| WO | 9534540 | 12/1995 |

OTHER PUBLICATIONS

Cervoni and Chan, Encycl. Of Chem. Tech., 4$^{th}$ ed., 8, 398–432 (1993).
Oliver et al., J. Physiol. (London), 18, 277–279 (1895).
du Vigneaud et al., J. Am. Chem. Soc., 76, 4751–4752 (1954).
Jackson, Pharm. Basis of Ther., 9$^{th}$ ed., 715–731 (1996).
Lethagen, Ann. Hematol., 69, 173–180 (1994).
Cash et al., Brit. J. Haematol, 27, 363–364 (1974).
David, Regulatory Peptides, 45, 311–317 (1993).
Burggraaf et al., Cli. Sci., 86, 497–503 (1994).
Manning et al., J. Med. Chem., 35, 382 (1992).
Manning et al., J. Med. Chem., 35, 3895 (1992).
Ruffolo et al., Drug News and Perspectives, 4(4), 217 (May 1991).
Albright et al., Curr. Pharm. Des., 3(6), 615 (1997).
Williams et al., J. Med. Chem., 35, 3905 (1992).
Huguenin et al., Helv. Chem. Acta, 49, 695 (1966) (translation).

*Primary Examiner*—Brenda Coleman
(74) *Attorney, Agent, or Firm*—Steven R. Eck

(57) ABSTRACT

The present invention provides compounds of the formula:

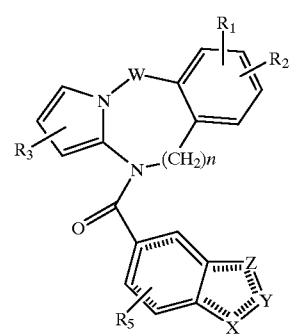

(I)

wherein:

X, Y and Z are independently selected from O, S, CH, $CH_2$, N, or $NR^4$;

W is moiety selected from $(CH_2)_n$;

n=1–2;

$R^1$, $R^2$ are independently, hydrogen, straight chain alkyl ($C_1$–$C_6$), branched chain alkyl ($C_3$–$C_7$), cycloalkyl ($C_3$–$C_7$), alkoxyalkyl ($C_2$–$C_7$), halogen, straight or branched chain alkoxy ($C_1$–$C_6$), hydroxy, $CF_3$, or perfluoroalkyl ($C_2$–$C_6$);

$R^3$ is hydrogen or a straight chain alkyl group ($C_1$–$C_6$), branched chain alkyl ($C_3$–$C_7$), cycloalkyl ($C_3$–$C_7$), alkoxyalkyl ($C_2$–$C_7$), or hydroxyalkyl ($C_1$–$C_6$);

$R^4$ is selected from hydrogen, or (lower alkyl ($C_1$–$C_6$); and $R_5$ is selected from halogen or hydrogen;

or a pharmaceutically acceptable salt thereof: as well as methods and pharmaceutical compositions utilizing these compounds for the treatment of disorder which may be remedied or alleviated by vasopressin agonist activity, including diabetes insipidus, nocturnal enuresis, nocturia, urinary incontinence, bleeding and coagulation disorders, or temporary delay of urination.

10 Claims, No Drawings

PYRROLOBENZODIAZEPINE CARBOXYAMIDE VASOPRESSIN AGONISTS

This application claims the benefit of U.S. Provisional Application No. 60/155,189, filed Feb. 4, 1999 now abandoned.

This invention concerns tricyclic benzoheterocyclic carboxyamides which act as vasopressin $V_2$ agonists, as well as methods of treatment and pharmaceutical compositions utilizing these compounds.

BACKGROUND OF THE INVENTION

Vasopressin (antidiuretic hormone, ADH) a nonapeptide hormone and neurotransmitter, is synthesized in the supraoptic nuclei of the hypothalamus of the brain and transported through the supraoptico-hypophyseal tract to the posterior pituitary where it is stored. Upon sensing an increase in plasma osmolality by brain osmoreceptors or a decrease in blood volume or blood pressure (detected by the baroreceptors and volume receptors), vasopressin is released into the blood circulation and activates vasopressin $V_{1a}$ receptors on blood vessels causing vasoconstriction to raise blood pressure; and vasopressin $V_2$ receptors of the nephron of the kidney causing reabsorption of water and to a lesser degree electrolytes, to expand the blood volume (Cervoni and Chan, Diuretic Agents, in Kirk-Othmer, Encyclopedia of Chemical Technology, 4th ed., Wiley, Volume 8, 398–432, (1993)). The existence of vasopressin in the pituitary was known as early as 1895 (Oliver and Schaefer, *J. Physiol.* (London), 18, 277–279, (1895)). The determination of the structure and the total synthesis of vasopressin were accomplished by du Vigneaud and coworkers in 1954 (du Vigneaud, Gish and Katsoyannis, *J. Am. Chem. Soc.*, 76, 4751–4752, (1954)).

The actions of vasopressin $V_{1a}$ receptors are mediated through the phosphatidylinositol pathway. Activation of vasopressin $V_{1a}$ receptors causes contraction of the smooth muscle of the blood vessels to raise blood pressure. The actions of the vasopressin $V_2$ receptors are mediated through activation of the adenylate cyclase system and elevation of intracellular levels of cAMP. The activation of vasopressin $V_2$ receptors by vasopressin or vasopressin-like (peptidic or non-peptidic) compounds increases water permeability of the collecting ducts of the nephron and permits the reabsorption of a large quantity of free water. The end result is the formation and excretion of a concentrated urine, with a decrease in urine volume and an increase in urinary osmolality.

Vasopressin plays a vital role in the conservation of water by concentrating the urine at the site of the collecting ducts of the kidney. The collecting ducts of the kidney are relatively impermeable to water without the presence of vasopressin at the receptors and therefore, the hypotonic fluid formed after filtering through the glomeruli, passing the proximal convoluted tubule, the loops of Henle, and the distal convoluted tubules, will be excreted as dilute urine. However, during dehydration, volume depletion or blood loss, vasopressin is released from the brain and activates the vasopressin $V_2$ receptors in the collecting ducts of the kidney rendering the ducts very permeable to water; hence water is reabsorbed and a concentrated urine is excreted. In patients and animals with central or neurogenic diabetes insipidus, the synthesis of vasopressin in the brain is defective and therefore, they produce no or very little vasopressin, but their vasopressin receptors in the kidneys are normal. Because they cannot concentrate the urine, they may produce as much as 10 times the urine volumes of their healthy counterparts and they are very sensitive to the action of vasopressin and vasopressin $V_2$ agonists. Vasopressin and desmopressin, which is a peptide analog of the natural vasopressin, are being used in patients with central diabetes insipidus. Vasopressin $V_2$ agonists are also useful for the treatment of nocturnal enuresis, nocturia, urinary incontinence and temporary delay of urination whenever desirable.

Vasopressin, through activation of its $V_{1a}$ receptors, exerts vasoconstricting effects so as to raise blood pressure. A vasopressin $V_{1a}$ receptor antagonist will counteract this effect. Vasopressin and vasopressin agonists release factor VIII and von Willebrand factor so they are useful for the treatment of bleeding disorders, such as hemophilia. Vasopressin and vasopressin-like agonists also release tissue-type plasminogen activator (t-PA) into the blood circulation so they are useful in dissolving blood clots such as in patients with myocardial infarction and other thromboembolic disorders (Jackson, "Vasopressin and other agents affecting the renal conservation of water", in Goodman and Gilman, *The Pharmacological Basis of Therapeutics*, 9th ed., Hadman, Limbird, Molinoff, Ruddon and Gilman Eds., McGraw-Hill, New York, pp. 715–731 (1996); Lethagen, Ann. Hematol. 69, 173–180 (1994); Cash et al., *Brit. J. Haematol.*, 27, 363–364 (1974); David, *Regulatory Peptides*, 45, 311–317 (1993); Burggraaf et al., *Cli. Sci.*, 86, 497–503 (1994)).

The following prior art references describe peptidic vasopressin antagonists: Manning et al., *J Med. Chem.*, 35, 382 (1992); Manning et al., *J. Med. Chem.*, 35, 3895 (1992); Gavras and Lammek, U.S. Pat. No. 5,070,187 (1991); Manning and Sawyer, U.S. Pat. No. 5,055,448 (1991); Ali, U.S. Pat. No. 4,766,108 (1988); Ruffolo et al., *Drug News and Perspectives* 4(4), 217 (May 1991); Albright and Chan, *Curr. Pharm. Des.* 3(6), 615 (1997). Williams et al., have reported on potent hexapeptide oxytocin antagonists [*J. Med. Chem.*, 35, 3905 (1992)] which also exhibit weak vasopressin antagonistic activity in binding to $V_1$ and $V_2$ receptors. Peptidic vasopressin antagonists suffer from a lack of oral activity and many of these peptides are non-selective antagonists since they also exhibit partial agonist activity.

Non-peptidic vasopressin antagonists have recently been disclosed. Albright et al. describe tricyclic azepines as vasopressin and oxytocin antagonists in U.S. Pat. No. 5,516,774 (1996); tetrahydrobenzodiazepine derivatives as vasopressin antagonists are disclosed in J. P. 0801460-A (1996); Ogawa et al., disclose benzoheterocyclic derivatives as vasopressin and oxytocin antagonists, and as vasopressin agonists in WO 9534540-A; and Venkatesan et al., disclose tricyclic benzazepine derivatives as vasopressin and oxytocin antagonists in U.S. Pat. No. 5,521,173 (1996).

As mentioned above, desmopressin (1-desamino-8-D-arginine vasopressin) (Huguenin and Boissonnas, *Helv. Chim. Acta*, 49, 695 (1966)) is a vasopressin agonist. The compound is a synthetic peptide with variable bioavailability. An intranasal route is poorly tolerated and an oral formulation for nocturnal enuresis requires a 10–20 fold greater dose than the intranasal administration.

Albright et al. broadly disclose a subset of tricyclic pyrrolo benzodiazepine indole carboxyamides of the present application, as $V_1$ and/or $V_2$ vasopressin receptor antagonists and oxytocin receptor antagonists in U.S. Pat. No. 5,512,563 (1996); U.S. Pat. No. 5,516,774 (1996); U.S. Pat. No. 5,624,923 (1997); U.S. Pat. No. 5,733,905 (1998); U.S. Pat. No. 5,736,540 (1998); EP 640592 A1 (1995); EP 0 636 625 A2 (1995), inter alia.

Compounds of general structure 16b in Scheme 4 of the above applications, are taught by Albright et al. to possess vasopressin and oxytocin receptors antagonist properties.

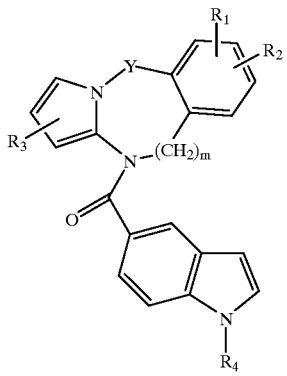

16b, Scheme 4
(Albright et al.)

wherein Y=(CH$_2$)$_n$ with n=0–2; and R$^4$=H, or lower alkyl (C$_1$–C$_3$).

However, the above indole carboxyamides of general structure 16b, have been found unexpectedly to be vasopressin V$_2$ receptor agonists in vivo, and thus possess different biological profile and clinical utility from those originally disclosed. Thus, rather than having an aquaretic effect, they unexpectedly cause reabsorption of water, i.e. they reduce urine volume and increase urine osmolality.

The compounds of this invention are non-peptidic and have a good oral bioavailability. They are vasopressin V$_2$ receptor agonists, and as such they promote reabsorption of water. They demonstrate no vasopressin V$_{1a}$ receptor agonist effects and, thus, do not raise blood pressure. In contrast, the prior art compounds (except some in WO 9534540-A) are described as vasopressin antagonists at both the V$_{1a}$ and V$_2$ receptors.

SUMMARY OF THE INVENTION

This invention relates to novel and known compounds selected from those of formula (I):

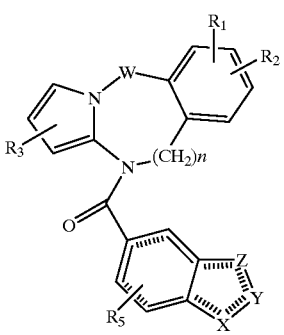

(I)

wherein:
X, Y and Z are independently selected from O, S, CH, CH$_2$, N, or NR$^4$;
W is moiety selected from (CH$_2$)$_n$;
n=1–2;
R$_1$, R$_2$ are independently, hydrogen, straight chain alkyl (C$_1$–C$_6$), branched chain alkyl (C$_3$–C$_7$), cycloalkyl (C$_3$–C$_7$), alkoxyalkyl (C$_2$–C$_7$), halogen, straight or branched chain alkoxy (C$_1$–C$_6$), hydroxy, CF$_3$, or perfluoroalkyl (C$_2$–C$_6$);
R$_3$ is hydrogen or a straight chain alkyl group (C$_1$–C$_6$), branched chain alkyl (C$_3$–C$_7$), cycloalkyl (C$_3$–C$_7$), alkoxyalkyl (C$_2$–C$_7$), or hydroxyalkyl (C$_1$–C$_6$);
R$_4$ is selected from hydrogen, or (lower alkyl (C$_1$–C$_6$); and
R$_5$ is selected from halogen or hydrogen;
or a pharmaceutically acceptable salt thereof.

Among the preferred moieties represented by the structure:

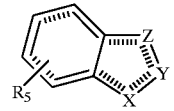

are the following:

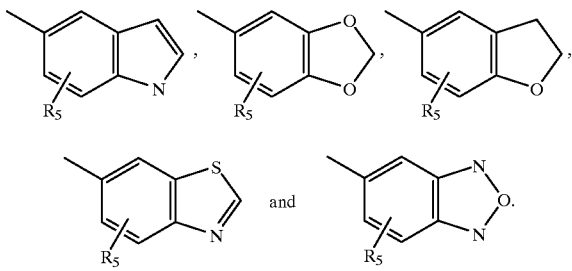

It is understood by those in the art that some of the compounds of this invention depending on the definition of R$_1$, R$_2$, R$_3$, and R$_4$ may contain one or more asymmetric centers and may thus give rise to optical isomers and diastereomers. The present invention includes such optical isomers and diastereomers; as well as the racemic and resolved, enantiomerically pure R and S stereoisomers, which possess the indicated activity. Optical isomers may be obtained in pure form by standard procedures known to those skilled in the art. It is also understood that this invention encompasses all possible regioisomers, and mixtures thereof which possess the indicated activity. Such regioisomers may be obtained in pure form by standard separation procedures known to those skilled in the art.

Also according to the present invention there is provided a method of treating, alleviating or preventing disorders which are remedied or alleviated by vasopressin receptor agonist activity. Methods of this invention for inducing vasopressin agonism in a mammal include, but are not limited to, methods for treating, alleviating or preventing diabetes insipidus, nocturnal enuresis, nocturia, urinary incontinence, bleeding and coagulation disorders, and temporary delay of urination whenever desirable in humans or other mammals, which comprises administering to a human or other mammal an effective amount of a compound or a pharmaceutical composition of the invention.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier or excipient.

The compositions are preferably adapted for oral administration. However, they may be adapted for other modes of administration, for example, parenteral administration for patients suffering from coagulation disorders.

In order to obtain consistency of administration, it is preferred that a composition of the invention is in the form of a unit dose. Suitable unit dose forms include tablets, capsules and powders in sachets or vials. Such unit dose forms may contain from 0.1 to 1000 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day. The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics and β-blocking agents.

Also according to the present invention there are provided processes for producing the compounds of the present invention.

PROCESS OF THE INVENTION

The compounds of the present invention of general formula (I) may conveniently be prepared according to the process shown in Scheme 1.

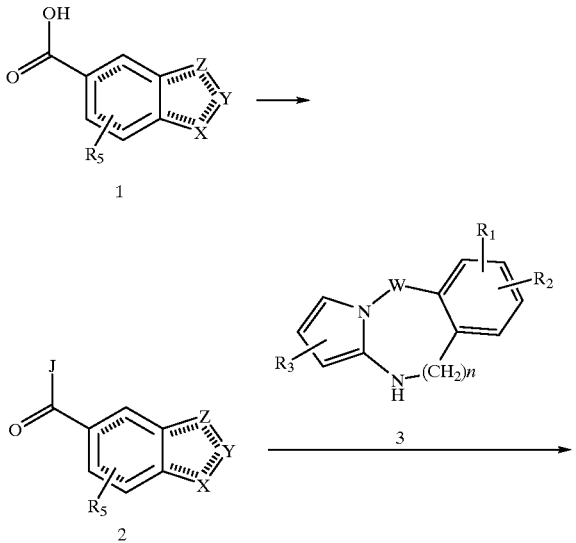

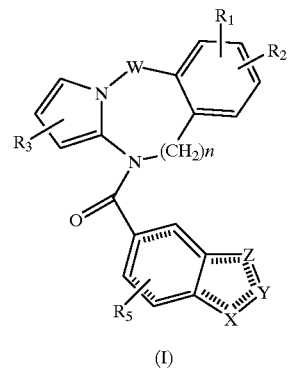

(I)

Thus, a pyrrolobenzodiazepine of formula (3, wherein W is $(CH_2)n$ and $n=1-2$, $R^1$, $R^2$, and $R^3$ are as defined above) is treated with an appropriately activated heteroaryl carboxylic derivative of formula (2) to provide the desired compounds of formula (I) wherein W, n, $R_1$, $R_2$, $R_3$, $R_4$, $R_5$, X, Y, and Z are as defined above.

The heteroaryl carboxylic acids of general formula (1) may be activated as their acid halides, preferably the chloride (2, J=Cl), and reacted with the pyrrolobenzodiazepine of formula (3) in the presence of an inorganic base such as potassium carbonate in a polar, aprotic solvent such as N,N-dimethylformamide; or an organic base such as 4-dimethylamino pyridine in an aprotic solvent, such as dichloromethane or tetrahydrofuran, at temperatures ranging from −40° C. to 50° C.

Alternatively, the acylating species of formula (2) can be a mixed anhydride of the corresponding carboxylic acid, such as that prepared by treating said acid with 2,4,6-trichlorobenzoyl chloride in an aprotic organic solvent such as dichloromethane, according to the procedure of Inanaga et al., Bull. Chem. Soc. Jpn., 52, 1989 (1979). Treatment of the mixed anhydride of general formula (2) with the pyrrolobenzodiazepine of formula (3) in an aprotic solvent such as dichloromethane and in the presence of an organic base such as 4-dimethylaminopyridine at temperatures ranging from 0° C. to the reflux temperature of the solvent, yields a compound of formula (I) wherein W, n, $R_1$, $R_2$, $R_3$, $R_4$, $R_5$, X, Y, and Z are as defined above.

Alternatively, the activation of the carboxylic acids of general formula (1) can be carried out by reacting said acids with other peptide coupling reagents known to those skilled in the art, in an organic aprotic solvent such as dichloromethane, tetrahydrofuran, N,N-dimethylformamide, or the like, at temperatures ranging from −40° C. to 120° C.

The activating reagent for the carboxylic acids of formula (1) is ultimately chosen on the basis of its compatibility with the $R^4$ and $R^5$ groups and its reactivity with the tricyclic pyrrolobenzodiazepine of formula (3).

The carboxylic acid intermediates (1) of Scheme 1 are either available commercially, or are known in the art, or can be readily prepared by procedures analogous to those in the literature for the known compounds.

The subject compounds of the present invention were tested for biological activity according to the following procedures.

Vasopressin V$_2$ Agonist Effects of Test Compounds in Normal Conscious Water-Loaded Rats:

Male or female normotensive Sprague-Dawley rats (Charles River Laboratories, Inc., Kingston, N.Y.) of 350–500 g body weight were supplied with standard rodent diet (Purina Rodent Lab. Chow 5001) and water ad libitum. On the day of test, rats were placed individually into metabolic cages equipped with devices to separate the feces from the urine and containers for collection of urine. A test compound or a reference agent was given at an oral dose of 10 mg/Kg in a volume of 10 mL/Kg. The vehicle used was 20% dimethylsulfoxide (DMSO) in 2.5% preboiled corn starch. Thirty minutes after dosing the test compound, rats were gavaged with water at 30 mL/Kg into the stomach using a feeding needle. During the test, rats were not provided with water or food. Urine was collected for four hours after dosing of the test compound. At the end of four hours, urine volume was measured. Urinary osmolality was determined using a Fiske One-Ten Osmometer (Fiske Associates, Norwood, Mass., 02062) or an Advanced CRYOMATIC Osmometer, Model 3C2 (Advanced Instruments, Norwood, Mass.). Determinations of Na$^+$, K$^+$ and Cl$^-$ ion were carried out using ion specific electrodes in a Beckman SYNCHRON EL-ISE Electrolyte System analyzer. The urinary osmolality should increase proportionally. In the screening test, two rats were used for each compound. If the difference in the urine volume of the two rats was greater than 50%, a third rat was used. The results of this study are shown in Table 1.

TABLE 1

| Example | Urine Volume (% decrease)[a] | Changes in Urinary Osmolality[b] | Rat Type[c] |
|---|---|---|---|
| 1 | 66 | 174 | CD |
| 2 | 23 | 41 | CD |
| 3 | 32 | 10 | CD |
| 4 | 19 | 3 | CD |

[a]Percent decrease in urine volume vs. control at a dose of 10 mg/Kg
[b]Osmolality changes expressed as percent of control at a dose of 10 mg/Kg
[c]Rat model used: Sprague-Dawley (CD)

The following examples are presented to illustrate rather than limit the scope of the invention.

EXAMPLE 1

(5H-10,11-Dihydro-pyrrolo [2,1-c][1,4] benzodiazepin-10-yl)-(1-methyl-1H-indol-5-yl)-methanone Step A. 1-Methyl-indole-5-carboxylic acid methyl ester Under an atmosphere of nitrogen, a solution of indole-5-carboxylic acid methyl ester (2.5 g, 14.3 mmol) in dry tetrahydrofuran (20 mL) was added dropwise to a stirred slurry of hexane-washed potassium hydride (1.63 g, 14.3 mmol, 35% in oil). When the hydrogen evolution ceased, iodomethane (1.3 mL, 21.5 mmol) was added to the stirred solution. After an additional 30 minutes at room temperature, the precipitate was filtered and washed with diethyl ether. The filtrate was concentrated in vacuo and the residue triturated with hexane to provide the title compound as a yellow solid (2.6 g).

NMR (CDCl$_3$, 400 MHz): δ 3.82 (s, 3H), 3.93 (s, 3H), 6.58 (dd, 1H), 7.10 (d, 1H), 7.32 (d, 1H), 7.92 (dd, 1H), 8.39 (s, 1H); MS (EI, m/z): 189 [M]$^+$, 158, 130.

Step B. 1-Methyl-indole-5-carboxylic acid

A solution of 1-methyl-indole-5-carboxylic acid methyl ester of Step A (2.5 g, 13.2 mmol) in ethanol (40 mL) containing 2.5N aqueous NaOH (3:1, v/v) was heated at reflux for one hour. The reaction mixture was concentrated in vacuo, and the residue partitioned between diethyl ether and 1N HCl. The organic layer was washed with brine, dried over sodium sulfate, and evaporated to dryness to provide the title compound as a off-white solid (1.82 g).

NMR (DMSO-d$_6$, 300 MHz): δ 3.82 (s, 3H), 6.58 (dd, 1H), 7.42 (d, 1H), 7.48 (d, 1H), 7.75 (d, 1H), 8.22 (s, 1H), 12.38 (broad s, 1H).

Step C. (5H-10,11-Dihydro-pyrrolo[2,1-c][1,4] benzodiazepin-10-yl)-(1-methyl-1H-indol-5-yl)-methanone Under anhydrous conditions, 2,4,6-trichlorobenzoyl chloride was added in one portion to a stirred solution of an equimolar amount of 1-methyl indole 5-carboxylic acid (0.327 g, 1.87 mmol) of Step B and triethylamine in dry tetrahydrofuran (0.1–0.3 molar). Upon completion of anhydride formation, the precipitate was filtered off and washed with tetrahydrofuran. The filtrate was concentrated in vacuo and the residue was dissolved in dichloromethane and added to a solution of equimolar amounts of the 10,11-dihydro-5H-pyrrolo[2,1c][1,4]-benzodiazepine (0.514 g, 2.8 mmol) and 4-dimethylamino pyridine in dichloromethane. Stirring was continued until the reaction was complete (TLC). The mixture was diluted with dichloromethane, washed sequentially with saturated aqueous sodium bicarbonate and brine, and dried over sodium sulfate. The solvent was evaporated, and the crude product was flash chromatographed (silica gel Merck-60, hexane/ethyl acetate 4:1) to provide pure title compound as a white solid (0.160g), m.p. 172–173° C., after recrystallization from diethyl ether.

NMR (DMSO-d$_6$, 400 MHz): δ 3.71 (s, 3H), 5.1 (broad s, 2H), 5.32 (broad s, 2H), 5.92 (m, 2H), 6.35 (m, 1H), 6.81 (m, 2H), 7.03 (m, 2H), 7.11 (m, 1H), 7.22 (d, 1H), 7.30 (d, 1H), 7.45 (dd, 1H), 7.55 (s, 1H); MS (EI, m/z): 341 [M]$^+$, 183, 158; Anal. Calcd. For C$_{22}$H$_{19}$N$_3$O: C, 77.40; H, 5.61; N, 12.31. Found: C, 76.87; H, 5.69; N, 12.42.

EXAMPLE 2

Benzo[1,3]dioxol-5-yl-(5H-10,11-dihydro-pyrrolo [2,1-c][1,4] benzodiazepin-10-yl)-methanone Under anhydrous conditions 2,4,6-trichlorobenzoyl chloride was added in one portion to a stirred solution of equimolar amounts of piperonylic acid (0.332 g, 2 mmol) and triethylamine in dry dichloromethane (25–50 mL). After anhydride formation was complete, the 10,11-dihydro-5H-pyrrolo[2,1c][1,4]-benzodiazepine (0.368 g, 2 mmol) and 4-dimethylamino pyridine were added to the clear solution. Stirring was continued until the reaction was complete (TLC). The reaction mixture was diluted with dichloromethane, washed sequentially with saturated aqueous sodium bicarbonate and brine, and dried over sodium sulfate. The solvent was evaporated and the crude product was flash chromatographed (silica gel Merck-60, hexane-ethyl acetate 4:1) to provide pure title compound as a white solid (0.179 g), m.p. 171° C., after recrystallization from diethylether.

NMR (DMSO-d$_6$, 400 MHz): δ 5.0–5.35 (broad s, 4H), 5.92 (m, 2H), 5.97 (s, 2H), 6.78 (m, 4H), 6.91 (d, 1H), 7.17 (m, 2H), 7.45 (d, 1H); MS (EI, m/z): 332 [M]$^+$, 149. Anal. Calcd. for C$_{20}$H$_{16}$N$_2$O$_3$: C, 72.28; H, 4.85; N, 8.43. Found: C, 71.70; H, 4.95; N, 8.17.

EXAMPLE 3

(2,3-Dihydro-benzofuran-5-yl)-(5H-10,11-dihydro-pyrrolo [2,1-c][1,4] benzodiazepin-10-yl)-methanone Prepared from 2,3-dihydro-benzofuran-5-carboxylic acid (0.328 g, 2 mmol) and 10,11-dihydro-5H-pyrrolo[2,1c][1, 4]-benzodiazepine (0.368 g, 2 mmol) in a manner essentially identical to that of Example 2. The title compound was obtained as a white solid (0.160 g), m.p. 161° C., upon recrystallization from diethyl ether.

NMR (DMSO-$d_6$, 400 MHz): δ 3.05 (t, 3H), 4.48 (t, 3H), 5.0–5.35 (broad s, 4H), 5.91 (m, 2H), 6.52 (d, 2H), 6.90 (dd, 2H), 7.15 (m, 2H), 7.22 (s, 1H), 7.45 (d, 1H); MS (EI, m/z): 330 [M]$^+$, 183, 147; Anal. Calcd. for $C_{21}H_{18}N_2O_2$: C, 76.34; H, 5.49; N, 8.48. Found: C, 76.24; H, 5.62; N, 8.39.

EXAMPLE 4

(Benzothiazol-6-yl)-(5H-10,11-dihydro-pyrrolo[2,1-c][1,4] benzodiazepin-10-yl)-methanone Step A. Benzothiazole-6-carbonyl chloride Under anhydrous conditions, a mixture of benzothiazole-6-carboxylic acid (1.0 g, 5.6 mmol) and oxalyl chloride (0.5 mL, 5.6 mmol) in dichloromethane (25 mL) containing a catalytic amount of N,N-dimethylformamide was stirred at ambient temperature for 3 hours. Removal of the solvent in vacuo provided a quantitative yield of the acid chloride as a light brown solid, which was used as such in the next step.

Step B. (Benzothiazol-6-yl)-(5H-10,11-dihydro-pyrrolo[2,1-c] [1,4] benzodiazepin-10-yl)-methanone Under an atmosphere of nitrogen, an equimolar mixture of the crude benzothiazole 6-carbonyl chloride of Step A (0.55 g, 2.78 mmol), 10,11-dihydro-5H-pyrrolo[2,1c][1,4]-benzodiazepine (0.49 g, 2.7 mmol) and potassium carbonate in N,N-dimethylformamide (10 mL) was stirred at ambient temperature for 1.5 hours. The reaction mixture was partitioned between water and ethyl acetate. The organic phase was washed with water and brine, and dried over sodium sulfate. Filtration of the solution through a thin pad of silica gel Merck-60 and evaporation of the filtrate to dryness provided the title compound as an oil which crystallized from diethyl ether as a white solid (0.495 g), m.p. 185–187° C.

NMR (DMSO-$d_6$, 400 MHz): δ 5.34 (broad, 2H), 5.92 (m, 2H), 6.83 (s, 1H), 6.92 (m, 1H), 7.01 (t, 1H), 7.12 (t, 1H), 7.37 (d, 1H), 7.45 (d, 1H), 8.17 (s, 1H), 9.40 (s, 1H); MS (EI. m/z): 345 [M]$^+$, 317, 183, 162.

EXAMPLE 5

(Benzo[2]oxa[1,3]diazol-5-yl)-(5H-10,11-dihydro-pyrrolo [2.1-c][1.4] benzodiazepin-10-yl)-methanone Under anhydrous conditions, a mixture of equimolar amounts of benzofurazan 5-carbonyl chloride (0.5 g, 2.75 mmol), 10,11-dihydro-5H-pyrrolo[2,1c][1,4]-benzodiazepine (0.5 g, 2.75 mmol) and triethylamine in dichloromethane was stirred at ambient temperature until reaction was complete (TLC). The reaction mixture was diluted with dichloromethane, washed sequentially with saturated aqueous sodium bicarbonate and brine, and dried over sodium sulfate. The residue remaining after removal of the solvent, was flash chromatographed (silica gel Merck-60, hexane-ethyl acetate 4:1) to provide the title compound as a white solid (0.370 g), m.p. 216–217° C., after recrystallization from dichloromethane-ethyl acetate.

NMR (DMSO-$d_6$, 400 MHz): δ 5.35 (broad, 4H), 5.91 (m, 1H), 5.99 (s, 1H), 6.84 (m, 1H), 7.10 (m, 3H), 7.45 (d, 1H), 7.47 (d, 1H), 7.93 (d, 1H), 7.98 (s, 1H); MS (EI, m/z): 330 [M]$^+$, 313, 183.

EXAMPLE 6

(6-Bromo-benzo[1,3]dioxol-5-yl)-(5H-10,11-dihydro-pyrrolo [2,1-c][1,4] benzodiazepin-10-yl)-methanone Under anhydrous conditions, to a solution of 6-bromo-1,3-benzodioxole-5-carboxylic acid (0.150 g, 0.61 mmol) in dichloromethane containing a catalytic amount of N,N-dimethylformamide, was added oxalyl chloride. (1.1 equivalents). When gas evolution ceased, the above solution was added in one portion to a solution of 10,11-dihydro-5H-pyrrolo[2,1c][1,4]-benzodiazepine (0.121 g, 0.65 mmol) and triethylamine (1 equivalent) in dichloromethane. The reaction mixture was diluted with dichloromethane, washed sequentially with saturated aqueous sodium bicarbonate and brine, and dried over sodium sulfate. The crude product obtained by evaporation of the solvent was flash chromatographed (over silica gel Merck-60, hexane-ethyl acetate 4:1) to provide pure title compound as an amorphous amber solid (0.085 g).

NMR (DMSO-$d_6$, 400 MHz): δ 5.27 (broad m, 4H), 5.88 (m, 1H), 5.98 (s, 3H), 6.80 (m, 1H), 6.92 (broad s, 1H), 7.10 (m, 3H), 7.36–7.39 (m, 2H); MS (EI, m/z): 410 [M]$^+$, 331, 227, 183.

What is claimed:

1. A compound of the formula (I):

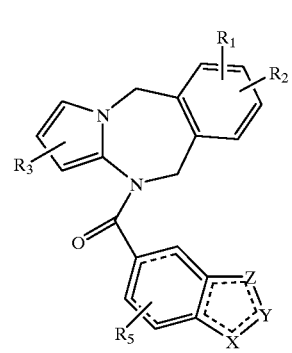

wherein:

$R_1$, $R_2$ are independently, hydrogen, straight chain alkyl ($C_1$–$C_6$), branched chain alkyl ($C_3$–$C_7$), cycloalkyl ($C_3$–$C_7$), alkoxyalkyl ($C_2$–$C_7$), halogen, straight or branched chain alkoxy ($C_1$–$C_6$), hydroxy, $CF_3$, or perfluoroalkyl ($C_2$–$C_6$);

$R_3$ is hydrogen or a straight chain alkyl group ($C_1$–$C_6$), branched chain alkyl ($C_3$–$C_7$), cycloalkyl ($C_3$–$C_7$), alkoxyalkyl ($C_2$–$C_7$), or hydroxyalkyl ($C_1$–$C_6$);

the moiety:

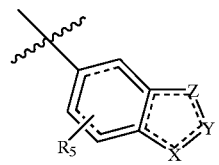

represents a moiety selected from the group of:

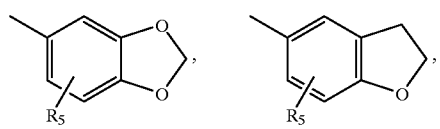

-continued

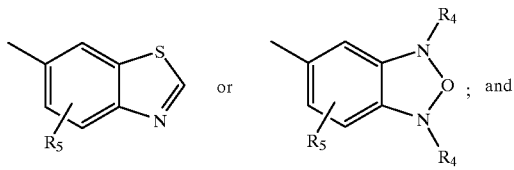

R$_4$ is selected from hydrogen, or lower alkyl (C$_1$–C$_6$);
R$_5$ is selected from halogen or hydrogen; or a pharmaceutically acceptable salt thereof.

2. A compound of claim 1 which is Benzo[1,3]dioxol-5-yl-(5H-10,11-dihydro-pyrrolo [2,1-c][1-4] benzodiazepin-10-yl)-methanone or a pharmaceutically acceptable salt thereof.

3. A compound of claim 1 which is (2,3-Dihydro-benzofuran-5-yl)-(5H-10,11-dihydro-pyrrolo [2,1-c][1,4] benzodiazepin-10-yl)-methanone or a pharmaceutically acceptable salt thereof.

4. A compound of claim 1 which is (Benzothiazol-6-yl)-(5H-10,11-dihydro-pyrrolo[2,1-c] [1,4] benzodiazepin-10-yl)-methanone or a pharmaceutically acceptable salt thereof.

5. A compound of claim 1 which is (Benzo[2]oxa[1,3]diazol-5-yl)-(5H-10,11-dihydro-pyrrolo [2,1-c][1,4] benzodiazepin-10-yl)-methanone or a pharmaceutically acceptable salt thereof.

6. A compound of claim 1 which is (6-Bromo-benzo[1,3]dioxol-5-yl)-(5H-10,11-dihydro-pyrrolo [2,1-c][1,4] benzodiazepin-10-yl)-methanone or a pharmaceutically acceptable salt thereof.

7. A method of treating disorders which are remedied or alleviated by vasopressin agonist activity in a mammal, the method comprising administering to the mammal in need thereof a pharmaceutically effective amount of a compound of the formula:

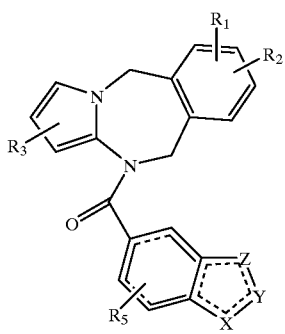

(I)

wherein:
R$_1$, R$_2$ are independently, hydrogen, straight chain alkyl (C$_1$–C$_6$), branched chain alkyl (C$_3$–C$_7$), cycloalkyl (C$_3$–C$_7$), alkoxyalkyl (C$_2$–C$_7$), halogen, straight or branched chain alkoxy (C$_1$–C$_6$), hydroxy, CF$_3$, or perfluoroalkyl (C$_2$–C$_6$);
R$_3$ is hydrogen or a straight chain alkyl group (C$_1$–C$_6$), branched chain alkyl (C$_3$–C$_7$), cycloalkyl (C$_3$–C$_7$), alkoxyalkyl (C$_2$–C$_7$), or hydroxyalkyl (C$_1$–C$_6$);

the moiety:

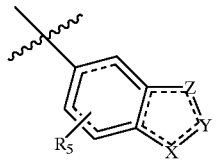

represents a moiety selected from the group of:

R$_4$ is selected from hydrogen, or lower alkyl (C$_1$–C$_6$); and R$_5$ is selected from halogen or hydrogen;
or a pharmaceutically acceptable salt thereof.

8. The method of claim 7 wherein the disorder which is remedied or alleviated by vasopressin agonist activity is selected from the group of diabetes insipidus, nocturnal enuresis, nocturia, urinary incontinence, bleeding and coagulation disorders, or temporary delay of urination.

9. The method of claim 7 wherein the compound is selected from the group of:

(5H-10,11-Dihydro-pyrrolo [2,1-c][1,4] benzodiazepin-10-yl)-(1-methyl-1H-indol-5-yl)-methanone;

Benzo[1,3]dioxol-5-yl-(5H-10,11-dihydro-pyrrolo [2,1-c][1-4] benzodiazepin-10-yl)-methanone;

(2,3-Dihydro-benzofuran-5-yl)-(5H-10,11-dihydro-pyrrolo [2,1-c][1,4] benzodiazepin-10-yl)-methanone;

(Benzothiazol-6-yl)-(5H-10,11-dihydro-pyrrolo[2,1-c] [1,4] benzodiazepin-10-yl)-methanone;

(Benzo[2]oxa[1,3]diazol-5-yl)-(5H-10,11-dihydro-pyrrolo [2,1-c][1,4] benzodiazepin-10-yl)-methanone; or (6-Bromo-benzo[1,3]dioxol-5-yl)-(5H-10,11-dihydro-pyrrolo [2,1-c][1,4] benzodiazepin-10-yl)-methanone;

or a pharmaceutically acceptable salt thereof.

10. A pharmaceutical composition comprising a pharmaceutically effective amount of a compound of claim 1, or a pharmaceutically acceptable salt thereof, and a pharmaceutically acceptable carrier.

* * * * *